United States Patent
Belisle et al.

(10) Patent No.: US 9,034,652 B2
(45) Date of Patent: May 19, 2015

(54) COLLOIDAL COOMASSIE STAIN

(71) Applicant: Bio-Rad Laboratories, Inc., Hercules, CA (US)

(72) Inventors: Christopher Belisle, Walnut Creek, CA (US); Lee Olech, Pinole, CA (US); Thomas Berkelman, Oakland, CA (US); Praveena Garimella, Fremont, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 14/205,182

(22) Filed: Mar. 11, 2014

(65) Prior Publication Data

US 2014/0273251 A1    Sep. 18, 2014

Related U.S. Application Data

(60) Provisional application No. 61/777,801, filed on Mar. 12, 2013.

(51) Int. Cl.
*G01N 33/68* (2006.01)

(52) U.S. Cl.
CPC ............ *G01N 33/6839* (2013.01); *G01N 33/68* (2013.01)

(58) Field of Classification Search
CPC .............. G01N 33/68; G01N 33/6803; G01N 33/6827; G01N 33/6839
USPC ................. 436/8, 17, 86, 164, 166, 174, 176; 252/408.1; 204/456, 462
See application file for complete search history.

(56) References Cited

U.S. PATENT DOCUMENTS

| | | | | |
|---|---|---|---|---|
| 4,023,933 | A * | 5/1977 | Bradford et al. | 436/87 |
| 4,239,495 | A * | 12/1980 | Gindler et al. | 436/86 |
| 2008/0145526 | A1 | 6/2008 | Mao et al. | |
| 2009/0131640 | A1 * | 5/2009 | Berkelman | 530/400 |
| 2011/0082089 | A1 * | 4/2011 | Borlak et al. | 514/19.3 |
| 2012/0190120 | A1 * | 7/2012 | Jones et al. | 436/86 |

OTHER PUBLICATIONS

Neuhoff et al. Electrophoresis, vol. 9, 1988, pp. 255-262.*
International Search Report and Written Opinion from PCT/US2014/023520, dated Jun. 6, 2014.

* cited by examiner

*Primary Examiner* — Maureen Wallenhorst
(74) *Attorney, Agent, or Firm* — Kilpatrick Townsend and Stockton LLP

(57) ABSTRACT

Colloidal formulation for staining proteins and methods of their use are provided.

8 Claims, 2 Drawing Sheets

COLLOIDAL COOMASSIE STAIN

CROSS-REFERENCE TO RELATED PATENT APPLICATIONS

The present application claims benefit of priority to U.S. Provisional Patent Application No. 61/777,801, filed Mar. 12, 2013, which is incorporated by referenced.

BACKGROUND OF THE INVENTION

The use of Coomassie Brilliant Blue G-250 for staining electrophoresis gels to a defined endpoint is possible because the dye can be formulated as a colloidal form that does not enter the gel for staining, but rather is adsorbed by the protein bands in the gel, saturating the bands given enough time to diffuse throughout the bands. The fact that the colloidal form does not enter the gel itself makes the background very low, and lowers the need for a destaining step, which can result in decreased intensity of the stained protein bands.

Typically, a two-part stain is used to stain electrophoesis gels. The two-part stain must be made fresh before each use to have the desired performance (e.g., low background). Two-part stains quickly form a precipitate that renders the solution unusable—typically in 24 hrs. Two-part stain formulations are also based on using methanol as the alcohol. Simply replacing methanol with ethanol will render the formulation to have unacceptable performance.

BRIEF SUMMARY OF THE INVENTION

Stabilized colloid stain formulations for staining proteins in electrophoresis gels are provided.

In some embodiments, the formulation comprises: Coomassie Brilliant Blue; a surfactant; ethanol; ammonium sulfate; and optionally orthophosphoric acid. In some embodiments, the Coomassie Brilliant Blue is Coomassie Brilliant Blue G-250 or Coomassie Brilliant Blue R-250. In some embodiments, the surfactant is poloxamer 407. In some embodiments, the formulation comprises 0.01-0.05% wt/wt Coomassie Brilliant Blue; 0.01-0.10% wt/wt poloxamer 407; 10-20% wt/wt ethanol; 5-10% wt/wt ammonium sulfate; and 0.5-5% orthophosphoric acid.

In some embodiments, the formulation comprises a Coomassie Brilliant Blue dye; a surfactant; ethanol or methanol; and ammonium sulfate. In some embodiments, the formulation further comprises orthophosphoric acid. In some embodiments, the formulation comprises ethanol (and in some further embodiments does not comprise methanol). In some embodiments, the formulation comprises methanol (and in some further embodiments does not comprise ethanol).

In some embodiments, the Coomassie Brilliant Blue is depicted in Formula 1. In some embodiments, the Coomassie Brilliant Blue is depicted in Formula 2.

In some embodiments, the surfactant is a polyoxyethylene-containing surfactant. In some embodiments, the surfactant is a poloxamer surfactant. In some embodiments, the surfactant is poloxamer 407.

In some embodiments, the formulation comprises: 0.01-0.05% wt/wt Coomassie Brilliant Blue dye; 0.01-0.10% wt/wt a surfactant; 10-20% wt/wt ethanol; 5-10% wt/wt ammonium sulfate; and 0.5-5% orthophosphoric acid. In some embodiments, the surfactant is a polyoxyethylene-containing surfactant. In some embodiments, the surfactant is a poloxamer surfactant. In some embodiments, the surfactant is a poloxamer 407.

Also provided are methods of staining proteins in an electrophoresis gel using the formulations described herein. In some embodiments, the method comprises contacting the gel with a formulation as described herein for a sufficient time and under conditions to stain proteins in the gel, and detecting the presence or quantity of protein in at least one region of the gel. In some embodiments, the formulation is stored at least three days before the contacting.

Also provided are methods of storing a colloidal formulation for proteins in an electrophoresis gel. In some embodiments, the method comprises storing the colloidal formulation as described herein for at least 3 (e.g., at least 7, 10, 15, 30, or more) days.

Also provided is a kit comprising the colloidal formulation as described herein.

DETAILED DESCRIPTION OF THE INVENTION

I. Introduction

Figure 1:
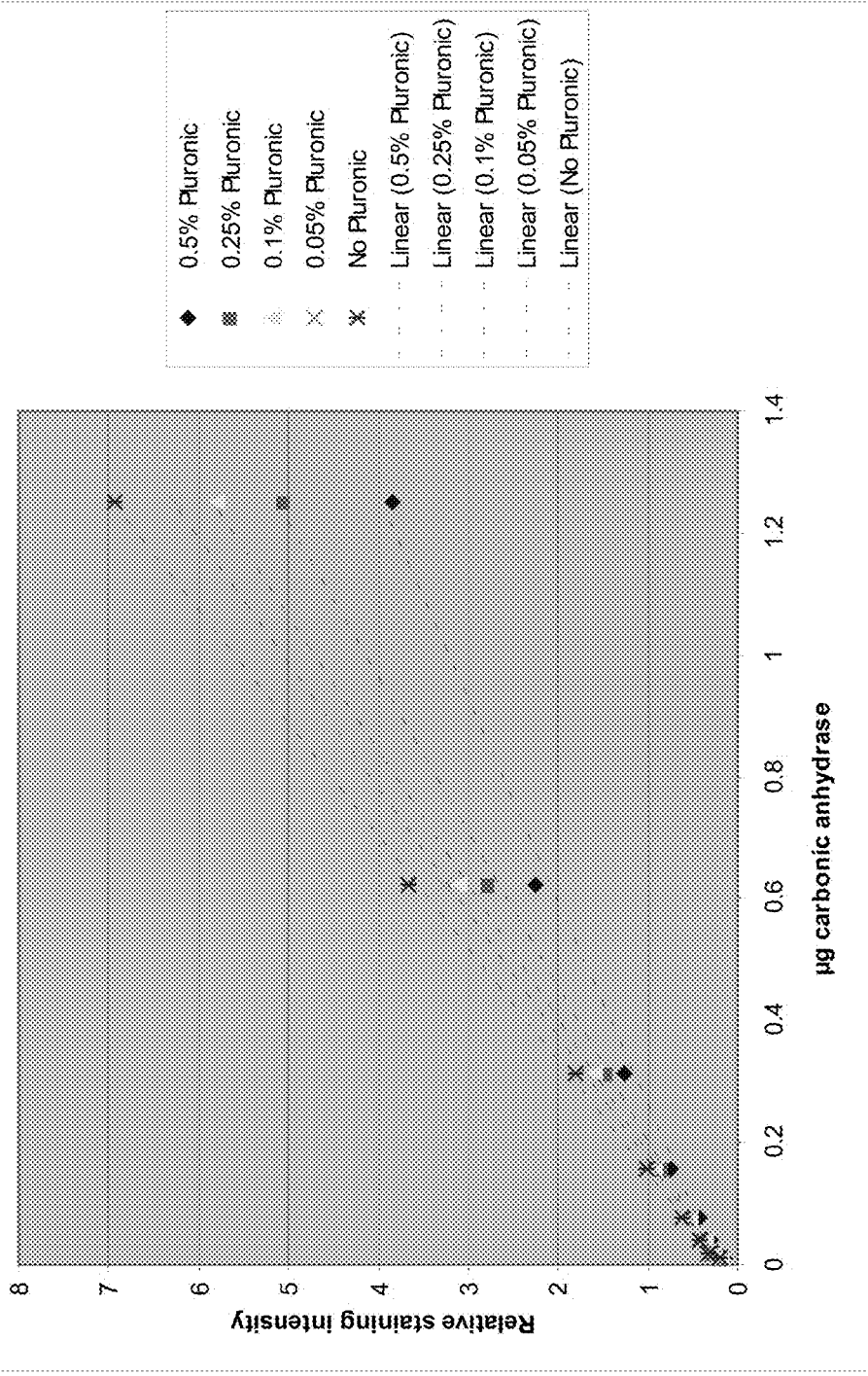
FIG. 1 illustrates the effect of various (0.5%-0.05%) Pluronic F-127 concentrations in staining formulations on staining intensity.

The inventors have discovered that a stable colloidal Coomassie Briliant Blue stain can be generated by including a surfactant and ethanol in the formulation. The resulting colloidal formulation i) has a long shelf-life, ii) is environmentally attractive (low environmental impact formulation using ethanol), and iii) is easier to use than a two-part stain because fewer steps are required to use the formulation. The formulations described herein perform essentially identically to a traditional 2-part short shelf life colloidal Coomassie stain (e.g., as described in Neuhoff et al., *ELECTROPHORESIS* 9(6):255-262 (1988).

The formulations described herein have at least two notable aspects. First, ethanol is used as the alcohol. The quantity of ethanol, as well as of ammonium sulfate, can be optimized for the increased solubility of Coomassie in EtOH vs. MeOH, thereby allowing for a stable colloidal Coomassie formulation.

Second, a surfactant (e.g., Pluronic™ F-127 (generically known as poloxamer 407)) is added to stabilize the formulation and prevent precipitation, thereby allowing for a long shelf-stable 1-part solution.

II. Components for Formulations

Colloidal dyes used for staining proteins can be used in the formulations described herein. Coomassie Brilliant Blue is a tradename for a class of dyes commonly used in protein staining Examples include Coomassie Brilliant Blue G-250 and Coomassie Brilliant Blue R-250. Coomassie Brilliant Blue R-250 is depicted below in Formula 1.

Formula 1

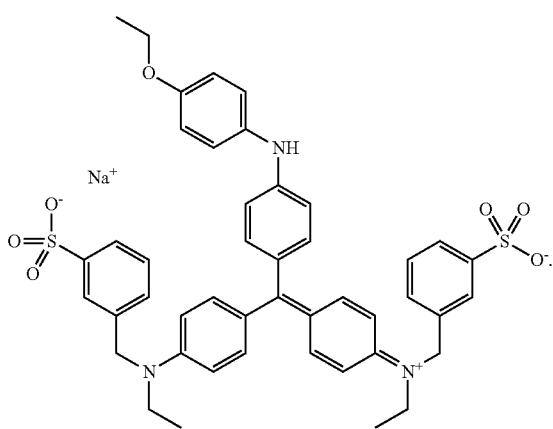

Coomassie Brilliant Blue G-250 (CAS number 6104-58-1) differs from R-250 by inclusion of two methyl groups as shown below in Formula 2.

Formula 2

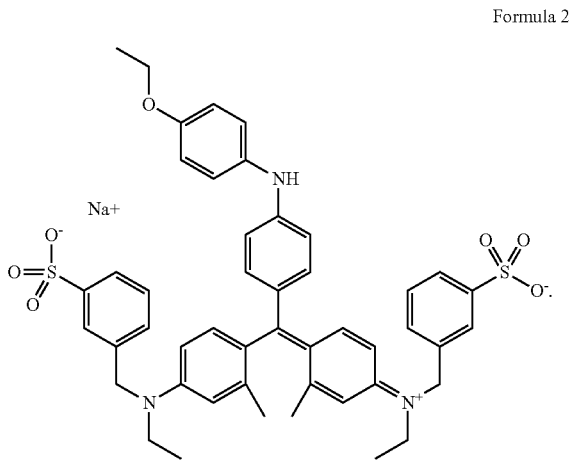

Generic terms for Coomassie Brilliant Blue R-250 (CAS number 6104-59-2) include Xylene Brilliant Cyanine G, as well as C.I. 42655, C.I. Acid Blue 90, Brilliant indocyanine G, and Brillantindocyanin G.

As noted above, the inclusion of a surfactant in the formulation provides for stability (e.g., lack of significant precipitation) of the formulation, allowing the formulation to be stored for long periods of time (e.g., based on accelerated shelf life studies, at least two years) prior to use. In view of the stability of the formulation, the formulation can be made as a "1-part" formulation (i.e., all staining ingredients in the same solution), thereby avoiding the step of preparing a fresh dye solution from a "2-part" formulation as is current practice in the industry. Without intending to limit the scope of possible surfactants that can be used in the formulations, in some embodiments, the surfactant is a polyoxypropylene-containing surfactant such as a poloxamer surfactant. Poloxamer surfactants are characterized by a central hydrophobic chain of polyoxypropylene (poly(propylene oxide)) flanked by two hydrophilic chains of polyoxyethylene (poly(ethylene oxide)). Because the lengths of the polymer blocks can be customized, many different poloxamers exist that have slightly different properties. Poloxamer copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic and Synperonic poloxamer tradenames, coding of these copolymers starts with a letter to define its physical form at room temperature (L=liquid, P=paste, F=flake (solid)) followed by two or three digits, The first digit (two digits in a three-digit number) in the numerical designation, multiplied by 300, indicates the approximate molecular weight of the hydrophobe; and the last digit×10 gives the percentage polyoxyethylene content (e.g., L61 indicates a polyoxypropylene molecular mass of 1,800 g/mol and a 10% polyoxyethylene content). In the example given, poloxamer 181 (P181)=Pluronic L61 and Synperonic PE/L 61. Exemplary poloxamer surfactants include, but are not limited to, Pluronuics F-127, F-108, F-68, P-105, L-35, and P-123. In other embodiments, the surfactant is a polyoxyethylene-containing surfactant, i.e., a surfactant comprising one or more polyoxyethyl groups.

The formulations will comprise an alcohol such as ethanol or methanol. Historically, methanol has been used stain formulations because standard formulations with ethanol had unacceptable performance issues. However, as discussed herein, the inclusion of a surfactant allows for inclusion of ethanol instead of methanol. The inclusion of ethanol instead of methanol is preferred in many instances because of the environmental and personal dangers of methanol. Nevertheless, in some embodiments, the formulation can contain methanol.

The ionic strength and pH of the formulation determine the colloidal properties of the stain formulation. Ionic strength can be controlled by addition of an ionic species at a level to provide for the desired colloidal properties of the stain. An exemplary ionic species is ammonium sulfate. Similarly, a weak acid can be included in the formulation to adjust and maintain the pH of the formulation. Exemplary acids include, but are not limited to, orthophosphoric acid, acetic acid, trichlororacetic acid (TCA) and protocatechuic acid (PCA). Additional considerations for generation of optimal conditions of ionic strength and pH can be found in, e.g., Neuhoff, et al., *Electrophoresis* 6:427-448 (1985); Neuhoff et al., *Electrophoresis* 11:101-117 (1990); and Neuhoff, et al., *Electrophoresis* 9:255-262 (1988).

The concentration of ingredients in the colloidal formulation can vary within a range, but the formulation that shows the best enhancement of stability, while maintaining the sensitivity of an unstabilized (i.e., standard 2-part methanol-based) formulation, is about 10-20% (e.g., 10, 11, 12, 13, 14, 15, 16, 17, 18, 19, or 20%) by weight of ethanol, about 5-10% (e.g., 5, 6, 7, 8, 9, or 10, e.g., between 7% and 8%) by weight of ammonium sulfate, about 0.01-0.10% (e.g., 0.01, 0.02, 0.03, 0.04, 0.05, 0.06, 0.07, 0.08, 0.09, or 0.10%) by weight surfactant (e.g., poloxamer 407, e.g., sold by BASF under the name Pluronic™ F-127) or other surfactants as described above), 0.01-0.05% (e.g., 0.01%, 0.02%, 0.03, 0.04, or 0.05%) by weight Coomassie Brilliant Blue (it is believed either of Coomassie Brilliant Blue R-250 or Coomassie Brilliant Blue G-250 can be used), and approximately 0.5-5% (e.g., 0.5, 1, 2, 3, 4, or 5%) by weight orthophosphoric acid. The formulation will be formulated in water, e.g., deionized water.

III. Methods

Any gel in which proteins have been electrophoresed can be stained with the formulations described herein according to standard staining protocols (e.g., by methods described in Sambrook et al., *Molecular Cloning—A Laboratory Manual*, Cold Spring Harbor Laboratory, Cold Spring Harbor, N.Y., (1989) or *Current Protocols in Molecular Biology*, Volumes 1-3, John Wiley & Sons, Inc. (1994-1998)). Examples of gels include, e.g., polyacrylamide and agarose gels. The formulations can also be used for gels in which the proteins have been separated by, e.g., isoelectric focusing and for 2-D gels. The matrix may also be a porous particle. Additionally, the invention can be used to stain proteins on and/or in membranes or filters made from natural or artificial materials such as cellulose or derivatized versions thereof (e.g., nitrocellulose) and nylon or derivatized versions thereof (e.g., PVDF). The protein may also be applied to the solid matrix or support by capillary action or wicking, chromatography, electrophoresis or electrofocussing, or other methods such as, for example, western blotting and immunoblotting.

EXAMPLE

A series of formulations were generated to make a stain that was safer and more stable than current methanol-based 2-part protein stains. An exemplary standard 2-part staining formulation comprised 8% ammonium sulfate, 1.6% orthophosphoric acid, 0.08% Coomassie Brilliant Blue G-250, and 20% methanol, formulated in deionized water. Initial attempts too simply replace the methanol with ethanol failed, producing a formulation with significant precipitates.

Figure 2:
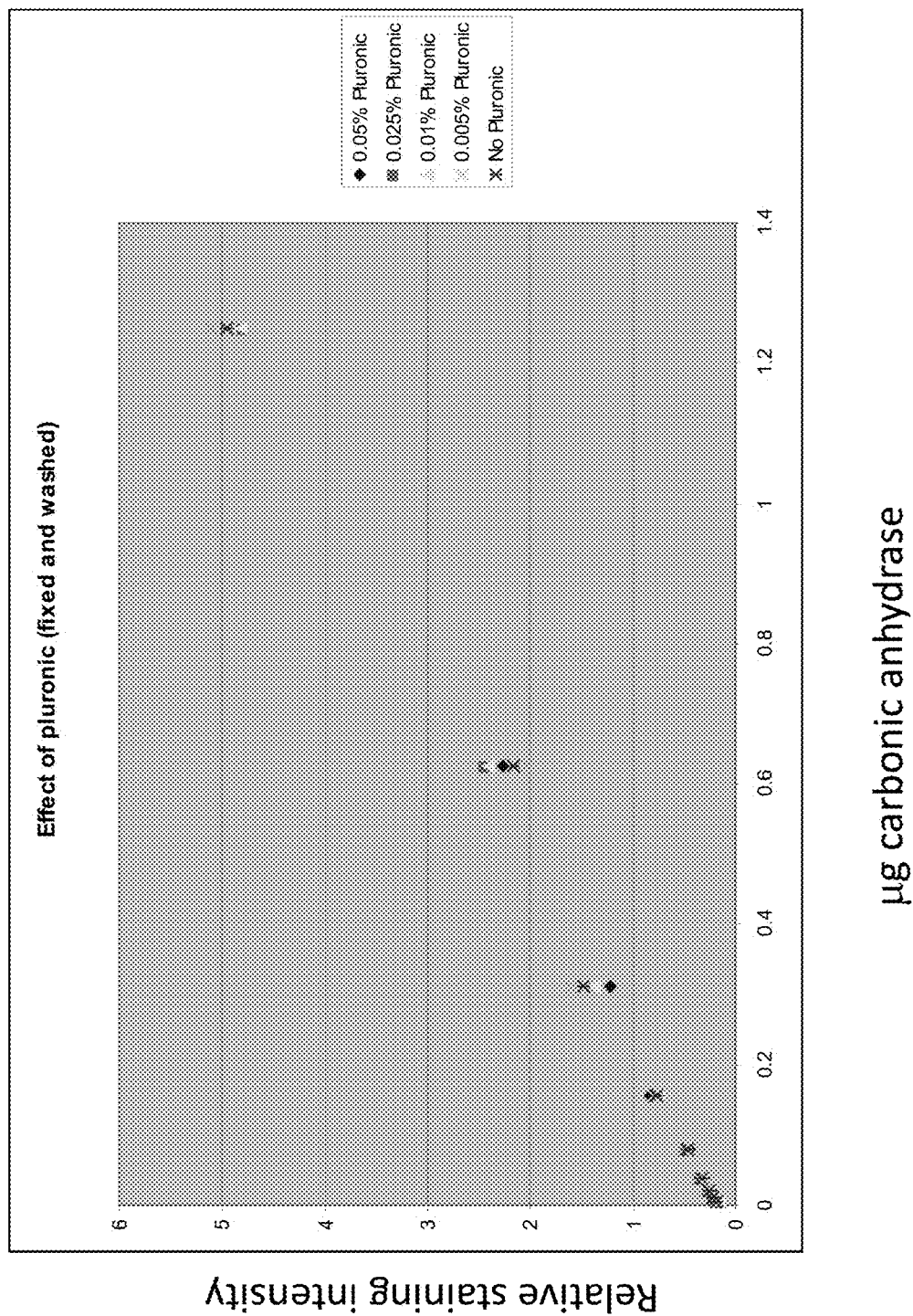
FIG. 2 illustrates the effect of various lower (0.05% and below) Pluronic F-127 concentrations in staining formulations on staining intensity.

Subsequently, the surfactant Pluronic F-127 was added to a formulation of Coomassie Brilliant Blue G-250 containing 7.8% ammonium sulfate, 2.2% orthophosphoric acid, and 14.2% ethanol. The formulation was prepared with various levels of Pluronic F-127 and the stain was stored in a covered dish for 5 days. Material was poured off and the remaining precipitate was visualized. Concentrations as low as 0.05% Pluronic F-127 prevented precipitates from forming. Further, the effect of surfactant concentration on relative protein staining was tested. The results are shown in FIG. 1-2 and show that the concentration of surfactant only had a minimal effect on protein (carbonic anhydrase) staining, especially at concentrations of Pluronic F-127 at or below 0.005% (FIG. 2).

An accelerated shelf life assay was performed with the formulation having 0.05% Pluronic F-127. The formulation was stored for 30 weeks at 37° C., and a second batch of the formulation was stored for 11 weeks at 50° C. Each of these stored formulations was then used to stain a protein polyacrylamide gel and generated acceptable results, i.e., equivalent to staining results of a freshly-made 2-part methanol-based stain.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A colloidal formulation for staining proteins in electrophoresis gels, the formulation comprising
   Coomassie Brilliant Blue;
   a surfactant;
   ethanol;
   ammonium sulfate; and optionally
   orthophosphoric acid.

2. The colloidal formulation of claim 1, wherein the Coomassie Brilliant Blue is Coomassie Brilliant Blue G-250 or Coomassie Brilliant Blue R-250.

3. The colloidal formulation of claim 1, wherein the surfactant is poloxamer 407.

4. The colloidal formulation of claim 1, comprising:
   0.01-0.05% wt/wt Coomassie Brilliant Blue;
   0.01-0.10% wt/wt poloxamer 407;
   10-20% wt/wt ethanol;
   5-10% wt/wt ammonium sulfate; and
   0.5-5% orthophosphoric acid.

5. A method of staining proteins in an electrophoresis gel, the method comprising,
   contacting the gel with the formulation of claim 1 for a sufficient time and under conditions to stain proteins in the gel, and
   detecting the presence or quantity of protein in at least one region of the gel.

6. The method of claim 5, wherein the formulation is stored at least three days before the contacting.

7. A method of storing a colloidal formulation for proteins in an electrophoresis gel, the method comprising,
   storing the colloidal formulation of claims 1 for at least 3 days prior to use for staining proteins in the gel.

8. A kit comprising the colloidal formulation of claim 1.

* * * * *